United States Patent [19]
Wojtowicz et al.

[11] 4,380,501
[45] Apr. 19, 1983

[54] GAS SCAVENGER AGENTS FOR CONTAINERS OF SOLID CHLOROISOCYANURATES

[75] Inventors: John A. Wojtowicz, Cheshire; Andree M. B. Gergo, East Haven, both of Conn.

[73] Assignee: Olin Corporation, New Haven, Conn.

[21] Appl. No.: 262,574

[22] Filed: May 11, 1981

[51] Int. Cl.$^3$ .................. C11D 3/48; C11D 3/24; C11D 3/395

[52] U.S. Cl. .................. 252/186.24; 252/90; 252/95; 252/181.5; 423/210; 8/109; 252/181.4; 252/186.35

[58] Field of Search ............ 252/90, 95, 181.4, 181.5, 252/187 C; 423/210; 8/109

[56] References Cited

U.S. PATENT DOCUMENTS 3,061,549 10/1962 Dickey .................. 252/90
3,183,057 5/1965 Marks et al. .............. 21/58
3,431,206 3/1969 Hilton et al. ............. 252/187 C
3,454,699 7/1969 Symes .................... 252/187 C
4,149,988 4/1979 Brennan et al. ........... 252/187 C Primary Examiner—John Kight, III
Assistant Examiner—Nathan M. Nutter
Attorney, Agent, or Firm—James B. Haglind; Donald F. Clements

[57] ABSTRACT

Chlorine-containing gases which may be formed in containers of solid chloroisocyanurates such as trichloroisocyanuric are adsorbed and decomposed by a gas scavenging agent consisting essentially of an alkaline earth metal sulfate, an alkali metal bicarbonate, and carbon. The gas scavenging agent is preferably contained in a gas permeable package which is enclosed in the container. The scavenging agent adsorbs mositure, adsorbs and decomposes nitrogen trichloride, removes chlorine, and neutralizes hydrogen chloride gases formed. Harmful build-up of noxious gases and the reduction of gas pressures within containers for solid chloroisocyanurates is achieved.

14 Claims, No Drawings

GAS SCAVENGER AGENTS FOR CONTAINERS OF SOLID CHLOROISOCYANURATES

This invention relates to improved packaging for chloroisocyanurate compositions used as dry sanitizing and disinfecting agents.

Chloroisocyanurates such as trichloroisocyanuric acid have a degree of instability which, for example, in the presence of moisture or heat results in their decomposition. This decomposition includes the evolution of highly noxious and otherwise objectionable gases such as nitrogen trichloride, chlorine, and mixtures thereof. U.S. Pat. No. 3,183,057 issued to H. C. Marks, R. R. Joiner and G. U. Glasgow teaches the generation of these gases from dry solid N-chloro compounds by their reaction with acidic and alkaline reagents in the presence of moisture. The reagents are enclosed in a moisture permeable envelope which allows sufficient moisture to initiate and sustain the reaction to evolve the gases. Water soluble acids and alkaline reagents are employed as reactants together with dichloroisocyanuric acid or trichloroisocyanuric acid. The envelope may contain as simple carriers or diluents inert substances such as calcium sulfate or magnesium sulfate.

It is frequently desirable, however, to produce packages for chloroisocyanurates in which the evolution of the pungent, nauseating chlorine-containing gases is inhibited by, for example, a deodorizing agent.

U.S. Pat. No. 2,897,154 issued to R. L. Low teaches the use of silver compounds such as silver nitrate, silver phosphate, silver oxide, or silver carbonates, as well as mercuric nitrate. These salts are expensive to employ, and in addition, the use of mercuric nitrate may impose a pollution problem.

Materials such as mixtures of manganese dioxide and cupric oxide, activated alumina, activated carbon, zeolites, bentonite, alkali metal silicates, alkali metal hydroxides, potassium, rubidium or cesium carbonates, or alkaline earth oxides are described as suitable deodorants in U.S. Pat. No. 3,061,549 issued to M. L. Dickey.

U.S. Pat. No. 4,146,578 issued Mar. 27, 1979, to J. P. Brennan, J. M. Casberg, and C. H. Putnam teaches decomposition inhibitors for solid chloroisocyanurates containing an alkaline earth metal sulfate or mixtures of an alkaline earth metal sulfate with an alkali metal bicarbonate or an alkali metal sulfite.

Further research into the mechanisms of the decomposition of solid chloroisocyanurates has shown that in addition to absorbing vapors formed during any decomposition of the solid chloroisocyanurates, it is desirable to convert these noxious gaseous decomposition products into innocuous gases.

Therefore there is need for an improved composition to inhibit and neutralize gases formed within containers of solid chloroisocyanurates.

It is an object of the present invention to provide a gas scavenger agent which is effective in preventing the accumulation of noxious gases in packages containing solid chloroisocyanurates.

An additional object of the present invention is to provide a gas scavenger agent which adsorbs and decomposes noxious gases such as nitrogen trichloride formed in packages containing solid chloroisocyanurates.

A further object of the present invention is to provide a scavenger agent which rapidly neutralizes acidic gases formed during decomposition of solid chloroisocyanurates.

These and other objects of the present invention are accomplished in a container of a solid chloroisocyanurate composition, the improvement which comprises enclosing therein a gas scavenging agent consisting essentially of an alkaline earth metal sulfate, an alkali metal bicarbonate, and carbon.

More in detail, solid chloroisocyanurate compositions include those containing trichloroisocyanuric acid, dichloroisocyanuric acid, salts of dichloroisocyanuric acid such as alkali metal dichloroisocyanurates and alkaline earth metal dichloroisocyanurates as well as complexes and mixtures thereof. Preferred solid chloroisocyanurate compositions are trichloroisocyanuric acid and alkali metal dichloroisocyanurates, with trichloroisocyanuric acid being particularly preferred. The solid chloroisocyanurates can be in any suitable form including granular or compressed forms such as tablets, rings, briquets, sticks, etc.

Solid chloroisocyanurate compositions are shipped and sold in a variety of containers including drums, bottles, cans, boxes, etc. The containers are closed, but are not completely sealed to allow escape of gases formed by any decomposition which might take place and prevent a buildup of gas pressure within the container.

Dry solid chloroisocyanurates are sensitive to moisture and heat and in their presence decomposition may take place resulting in the formation of noxious gases including chlorine, nitrogen trichloride, and often hydrogen chloride. While the exact mechanism of noxious gas formation within the containers of solid chloroisocyanurates is unknown, and not wishing to be bound by theory, it is believed that moisture present in the product or entering the container hydrolyzes the chloroisocyanurate to initially form hypochlorous acid. Hypochlorous acid reacts with additional chloroisocyanurate to produce nitrogen trichloride. Subsequent decomposition of nitrogen trichloride forms chlorine. Carbon dioxide gas is also formed during the decomposition of solid chloroisocyanurates. While not reactive with the compounds, its presence increases the gas pressure within the container. Hydrogen chloride is believed to be formed by the reaction of chlorine present with certain packaging materials, for example, polyolefins.

The novel gas scavenging composition of the present invention interacts with these decomposition products to decompose nitrogen trichloride to chlorine and nitrogen gases, absorb the chlorine formed, and neutralize any hydrogen chloride which is formed.

The gas scavenging composition of the present invention consists essentially of a mixture of an alkaline earth metal sulfate, an alkali metal bicarbonate, and carbon. Each of these ingredients is employed in a particulate form of the solid.

Suitable alkaline earth metal sulfates used in the gas scavenging compositions include calcium sulfate or magnesium sulfate. Magnesium sulfate is a preferred embodiment because of its superior moisture absorbing properties. Where the gas scavenging composition is contained in a gas permeable package, the particle size of the alkaline earth metal sulfate is selected to be sufficiently large to prevent leakage through or plugging of the pores of the package material. When the composition is distributed loosely throughout the container of the solid chloroisocyanurate, suitable particle sizes are those, for example, in the range of from about 40 to about 4000, and preferably from about 70 to about 2000 microns. The anhydrous form of the alkaline earth metal sulfate is preferred, however, lower hydrates such as magnesium sulfate monohydrate may be used to provide coarser particles.

Alkali metal bicarbonates which can be employed in the gas scavenging compositions include sodium bicarbonate or potassium bicarbonate, with sodium bicarbonate being a preferred embodiment. Alkali metal bicarbonates remove and inactivate chlorine and hydrogen chloride gases. Suitable particle sizes for the anhydrous bicarbonate particles include those in the range of from about 40 to about 300 and preferably from about 80 to about 200 microns.

The third ingredient of the gas scavenging composition, carbon, is employed as substantially anhydrous porous particles which may be either unactivated or activated, with activated carbon particles being preferred. Carbon granules employed are those having substantial amounts of internal and external surface area which adsorb chlorine and carbon dioxide and promote the decomposition of nitrogen trichloride. The granules may have any suitable particle sizes, for example, those in the range of from about 100 to about 2000 microns, and preferably from about 200 to about 1700 microns.

The carbon particles may be coated or impregnated with metal salts such as those of copper, nickel, cobalt, and chromium including, for example, the chlorides, sulfates, nitrates, oxides, or hydroxides of these metals. Preferred as coatings or impregnants are metal salts of cobalt, nickel, or copper which are more soluble in water such as cobalt chlorides, cobalt sulfates, cobalt nitrates, nickel chlorides, nickel sulfates, nickel nitrates, copper chlorides, copper sulfates, copper nitrates, and mixtures thereof with cobalt chlorides, nickel chlorides, copper chlorides, and mixtures thereof being particularly preferred.

The gas scavenging compositions of the present invention may include a wide range of component ratios to effectively remove and inactivate noxious chlorine-containing gases. Suitably the gas scavenging compositions contain at least 5 percent by weight of each of the components. Preferably, the alkaline earth metal sulfate, the alkali metal bicarbonate, and carbon are each present in at least 10 percent by weight. More preferably, the gas scavenging composition of the present invention contains at least 20 percent by weight of each of the three components. For example, where the solid chloroisocyanurate is trichloroisocyanuric acid, the gas scavenging composition may contain preferably at least 10 percent by weight of carbon and the alkaline earth metal sulfate and the alkali metal bicarbonate each in amounts in the range of from about 10 to about 80 percent by weight. When the solid chloroisocyanurate is an alkali metal salt of dichloroisocyanuric acid such as sodium dichloroisocyanurate dihydrate, the portion of alkaline earth metal sulfate can be reduced and preferred component weight ratios include those in which the alkaline earth metal sulfate is at least 10 percent by weight and the alkali metal bicarbonate and carbon are each present in amounts in the range of from about 10 to about 80 percent by weight. The cumulative total being, of course, no greater than 100 percent.

The novel gas scavenging compositions of the present invention may be admixed directly with the solid chloroisocyanurate, for example, by introducing the compositions into the container. Where this method is used the solid chloroisocyanurate is preferably in a compressed form such as that of a tablet, stick, or briquet.

In a preferred embodiment, the gas scavenging composition is enclosed in a gas permeable package which is deposited in the container of solid chloroisocyanurate. The package is suitably made of any chlorine-resistant material and whose permeability permits the admission of $Cl_2$, $NCl_3$, $CO_2$, and $N_2$ gases and moisture vapor while preventing leakage of the particulate components of the scavenging composition. Suitable materials include, for example, polyolefins such as polyethylene and polypropylene, polyesters, and polyvinyl chloride in film or fabric form.

Considerable savings on materials result where the gas scavenging compositions are enclosed in a package as only about 50 percent as much is required as where the gas scavenging composition is directly admixed with the solid chloroisocyanurate.

Any amounts of the gas scavenging compositions may be employed which will effectively remove moisture and render innocuous noxious gases which may be formed. For example, commercially produced trichloroisocyanuric acid has a moisture content of about 0.2 percent and preferably less than 0.1 percent by weight of water. Suitable amounts of the gas scavenging compositions admixed with commercial trichloroisocyanuric acid include those in the range of from about 0.5 to about 10, preferably from about 0.8 to about 6, and more preferably from about 1 to about 4 percent by weight of said trichloroisocyanuric acid.

Packages of the gas scavenging compositions of the present invention may also be used in containers of products including solid chloroisocyanurates as a component. For example, containers of detergent mixtures, sanitizing compositions, cleansing agents, and bleaching compositions in which solid chloroisocyanurates are used as a source of available chlorine are protected from damage and the release of noxious chlorine-containing gases by the inclusion of a package of the novel gas scavenging compositions of the present invention.

Suitable packages of these compositions may also be used in air filtering or purifying equipment which is employed in areas in which chlorine-containing gases such as nitrogen trichloride are produced.

The novel gas scavenging compositions of the present invention when enclosed in containers of solid chloroisocyanurates effectively inhibit the accumulation or release of moisture in the container. Chlorine-containing gases such as chlorine are adsorbed while nitrogen trichloride is both adsorbed and decomposed. Further, the gas scavenging compositions neutralize acidic gases such as hydrogen chloride which may be formed. Containers for solid chloroisocyanurates enclosing the gas scavenging compositions can be sealed more tightly as the accumulation of gases in the container and hence the internal gas pressure is significantly reduced. A tighter seal reduces the amount of moisture vapor and atmospheric gases which can enter the container. If the container's seal is defective, the gas scavenging compositions will prevent excessive decomposition of the solid chloroisocyanurates contained within.

Employing the novel gas scavenging composition prevents embrittlement of the container itself as well as inhibiting bleaching of container components such as caps and labels.

The novel gas scavenging compositions of the present invention are further illustrated by the following examples without any intention of being limited thereby. All percentages are by weight unless otherwise specified.

EXAMPLE 1

A mixture was prepared of commercial grade anhydrous magnesium sulfate, commercial grade anhydrous sodium bicarbonate, and activated carbon particles having a particle size in the range of 14 to 40 mesh. The carbon particles had been immersed in an aqueous solution of a mixture of $CuCl_2$, $NiCl_2$, and $CoCl_2$ and dried. The dried carbon particles contained 0.4 percent each of $CuCl_2$, $NiCl_2$, and $CoCl_2$. The mixture (28 grams) containing 18 percent by weight of magnesium sulfate, 64 percent by weight of sodium carbonate, and 18 percent by weight of carbon particles was added to a small glass beaker. The beaker was placed in an upright position near the top of a plastic container holding 1816 grams of trichloroisocyanuric acid tablets. The plastic container was sealed with a bright orange screw cap having a polyethylene foam liner. The plastic container enclosing the beaker of gas scavenger agent was placed in a room whose atmosphere was controlled at a temperature of 110° F. and 55 percent relative humidity. Samples of gas decomposition products were taken periodically by piercing the upper part of the container with a hypodermic needle, withdrawing a 1 cc sample of gas, and resealing the opening. The gas sample was analyzed by gas chromatography for nitrogen trichloride and chlorine. A visual inspection was also made of the orange bottle cap to ascertain evidence of bleaching. Bleaching of the top of the orange cap was found to have occurred after a period of 235 days. Analytical results are given in TABLE I below.

COMPARATIVE EXAMPLES A–E

The procedure of EXAMPLE 1 was repeated using as scavenging agents 28 grams of each of the following: anhydrous sodium bicarbonate; anhydrous magnesium sulfate; a mixture of sodium bicarbonate and magnesium sulfate in equal amounts; activated carbon containing 0.4 percent each of $CuCl_2$, $NiCl_2$, and $CoCl_2$; and anhydrous activated carbon. The carbon particles had a particle size in the range of 14 to 40 mesh. A glass beaker of each of these scavenging agents was placed inside a plastic container identical to that of EXAMPLE 1 holding 1816 grams of trichloroisocyanuric acid tablets and sealed with an orange plastic top having a poly foam liner. A plastic container of trichloroisocyanuric acid tablets having no scavenging agent was used as the control. Each of these plastic containers was placed in the controlled atmosphere room in which the identical conditions of temperature (110° F.) and humidity (55% RH) employed in EXAMPLE 1 were maintained. Gases formed by decomposition of the trichloroisocyanuric acid tablets were analyzed periodically by the method of EXAMPLE 1. A visual observation was also made of the bleaching of the orange cap. The results for COMPARATIVE EXAMPLES A–E are reproduced in TABLE 1 below.

TABLE I

GAS SCAVENGERS FOR CONTAINERS OF TRICHLOROISOCYANURIC ACID TABLETS
GAS ANALYSIS (%)

| EXAMPLE (28 grams) | 14 Days $Cl_2$ | 14 Days $NCl_3$ | 14 Days Total | 28 Days Total | 56 Days Total | 83 Days Total | Cap Bleached (Days) |
|---|---|---|---|---|---|---|---|
| 1. $MgSO_4$/$NaHCO_3$/C 5:18:5 | 0.01 | 0.01 | 0.02 | 0.01 | 0.00 | 0.00 | 235 |
| Control | 3.44 | 0.87 | 4.31 | 3.05 | 0.88 | 0.83 | 7 |
| Comparative Example A $NaHCO_3$ | 0.15 | 1.38 | 1.53 | 0.48 | 0.08 | 6.71 | 14 |
| Comparative Example B $MgSO_4$ | 0.43 | 0.00 | 0.43 | 0.33 | 0.14 | 0.14 | 70 |
| Comparative Example C $NaHCO_3$/$MgSO_4$ 14:14 | 0.03 | 0.21 | 0.24 | 0.27 | 0.06 | 0.49 | 70 |
| Comparative Example D Carbon (treated) | 0.01 | 0.00 | 0.01 | 0.01 | 0.15 | 3.70 | 70 |
| Comparative Example E carbon (untreated) | 0.01 | 0.00 | 0.01 | 0.35 | 3.81 | — | 56 |

As shown in TABLE 1 above, the novel gas scavenger agent of the present invention is highly efficient in controlling the amounts of $NCl_3$ and $Cl_2$ found in the head gas samples from the containers so that only minimal amounts are present. In contrast, the control and COMPARATIVE EXAMPLES permit considerable amounts of the chlorine-containing gases to accumulate resulting in bleaching of package components such as the container cap as well as embrittlement and weakening of the polyethylene containers themselves. The gas scavenging composition of the present invention is surprisingly superior to the individual components of the mixture as shown by the results of EXAMPLE 1 when contrasted with that of COMPARATIVE EXAMPLES A–E.

EXAMPLE 2

A mixture of anhydrous commercial grade magnesium sulfate, anhydrous commercial grade sodium bicarbonate and activated carbon was prepared in a weight ratio of 41 percent of $MgSO_4$ to 41 percent of $NaHCO_3$ to 18 percent of C. The mixture (56 grams) was added directly to a plastic container holding 1816 grams of trichloroisocyanuric acid (TCCA) tablets. An identical container holding 4 pounds of TCCA tablets, but having no gas scavenging composition was used as the control. While stored in a controlled atmosphere maintained at 100° F. and a relative humidity of 85 percent, gases produced by decomposition of the TCCA were analyzed periodically by the method of EXAMPLE 1. Gas analysis results are recorded in TABLE 2. After a period of 203 days, the orange color in the top of the cap of the container of EXAMPLE 1 was found to be bleached out. The top of the cap of the container used as the control had been bleached in only 14 days.

EXAMPLES 3-4

Using the mixture of EXAMPLE 2, two gas permeable polypropylene scrim packets were each filled with 28 grams. The packets were heat sealed along the top edge and each placed in a plastic container of TCCA tablets (1816 grams). The packet of EXAMPLE 3 was placed near the top of the container of TCCA tablets. In EXAMPLE 4, the packet was placed at the bottom of the container. As the control, an identical container of TCCA tablets enclosing a polypropylene scrim packet, but without a gas scavenging composition was used. Gases formed by decomposition of the TCCA tablets were measured periodically using the method of EXAMPLE 1. Gas analysis results are recorded in TABLE 2 below.

TABLE II

GAS SCAVENGERS FOR CONTAINERS OF TRICHLOROISOCYANURIC ACID TABLETS
GAS ANALYSIS (%) $Cl_2$ + $NCl_3$

| Example No. | Initial | 16 | 34 | 51 | 105 | 118 | 150 | 164 | 183 | 203 | Cap Bleached (Days) |
|---|---|---|---|---|---|---|---|---|---|---|---|
| 2. $MgSO_4$/$NaHCO_3$/C (56 g.) 41%  41%  18% | — | 0.00 | 0.00 | 0.00 | 0.02 | 1.74 | 2.98 | 4.23 | 7.33 | | 203 |
| Control | 17.15 | 6.47 | 2.42 | 4.9 | 2.83 | 2.54 | 2.56 | | | | 16 |
| 3. $MgSO_4$/$NaHCO_3$/C (28 g.) 41%  41%  18% (polypropylene packet at top of container) | — | 0.00 | 0.00 | 14.6 | 10.75 | 6.21 | | | | | 118 |
| 4. $MgSO_4$/$NaHCO_3$/C (28 g.) 41%  41%  18% (polypropylene packet at bottom of container) | — | — | 0.00 | trace | 7.69 | 3.83 | | | | | 150 |
| 5. Control (polypropylene packet only) | 16.10 | — | 3.10 | 5.3 | 2.98 | 1.93 | | | | | 16 |

EXAMPLES 5-7

Three mixtures of anhydrous magnesium sulfate, anhydrous sodium bicarbonate and activated carbon were prepared having various weight ratios of the components. The weight ratios of $MgSO_4$/$NaHCO_3$/C were 33%:33%:33%; 18%:64%:18%; and 41%:41%18%. Polypropylene scrim packets were filled with 7 grams, 14 grams and 28 grams of each of the mixtures, sealed and enclosed in polyethylene containers holding 1816 grams of TCCA tablets. The containers were stored in a controlled atmosphere maintained at 100° F. and 85 percent relative humidity. Using the method of EXAMPLE 1, head gas analyses determined the percentage of $NCl_3$ and $Cl_2$ present after 14 days. The results are as follows:

| Example No. | Wt. of Mixture (grams) | Wt. Ratio of $MgSO_4NaHCO_3$/C (%) | | |
|---|---|---|---|---|
| | | 33:33:33 | 18:64:18 | 41:41:18 |
| | | Gas Analysis (% $NCl_3$ + $Cl_2$) | | |
| 5 | 7 | 16.9 | 13.3 | 12.2 |
| 6 | 14 | 14.7 | 7.0 | 0.5 |
| 7 | 28 | 0.02 | 0.10 | 0.03 |

What is claimed is:

1. In a container of a solid chloroisocyanurate composition, the improvement which comprises enclosing therein a gas scavenging agent consisting essentially of a mixture of an alkaline earth metal sulfate, an alkali metal bicarbonate, and carbon.

2. The container of claim 1 in which said solid chloroisocyanurate is selected from the group consisting of trichloroisocyanuric acid, dichloroisocyanuric acid, alkali metal salts of dichloroisocyanuric acid, alkaline earth metal salts of dichloroisocyanuric acid, and mixtures thereof.

3. The container of claim 2 in which said gas scavenging composition is contained in a sealed, gas permeable package.

4. The container of claim 3 in which said mixture comprises at least 5 percent by weight of each of said alkaline earth metal sulfate, said alkali metal bicarbonate, and said carbon.

5. The container of claim 4 in which said alkali metal bicarbonate is anhydrous sodium bicarbonate.

6. The container of claim 5 in which said alkaline earth metal sulfate is selected from the group consisting of calcium sulfate and magnesium sulfate and lower hydrates thereof.

7. The container of claim 6 in which said carbon is activated carbon.

8. The container of claim 7 in which said solid chloroisocyanurate is trichloroisocyanuric acid.

9. The container of claim 8 in which the amount of said gas scavenging agent is from about 0.5 to about 10 percent by weight of said solid chloroisocyanurate.

10. The container of claim 9 in which compressed form of said solid chloroisocyanurate is selected from the group consisting of tablets, rings, briquets, and sticks.

11. The container of claim 10 in which said alkaline earth metal sulfate is magnesium sulfate.

12. The container of claim 11 in which said mixture comprises at least 10 percent by weight of each of said alkaline earth metal sulfate, said alkali metal bicarbonate, and said carbon.

13. The container of claim 2 in which said carbon is coated with a metal salt selected from the group consisting of copper salts, cobalt salts, nickel salts, chromium salts, and mixtures thereof.

14. A gas scavenging agent for scavenging gases containing nitrogen trichloride which consists essentially of a gas permeable package enclosing a mixture of an alkaline earth metal sulfate, an alkali metal bicarbonate, and carbon.

* * * * *